United States Patent [19]

Miwa

[11] 4,452,082
[45] Jun. 5, 1984

[54] ULTRASONIC MEASURING METHOD

[75] Inventor: Hirohide Miwa, Kawasaki, Japan

[73] Assignee: Fujitsu Limited, Kawasaki, Japan

[21] Appl. No.: 372,547

[22] Filed: Apr. 28, 1982

[30] Foreign Application Priority Data

Apr. 30, 1981 [JP] Japan .................................. 56-65536

[51] Int. Cl.³ ............................................ G01N 29/00
[52] U.S. Cl. ......................................... 73/599; 73/602
[58] Field of Search ................................... 73/599, 602

[56] References Cited

U.S. PATENT DOCUMENTS

| | | | |
|---|---|---|---|
| 3,815,409 | 6/1974 | Macovski | 73/625 |
| 3,996,791 | 12/1976 | Niklas et al. | 73/602 |
| 4,016,750 | 4/1977 | Green | 73/631 |
| 4,063,549 | 12/1977 | Beretsky et al. | 73/602 |
| 4,176,658 | 12/1979 | Kossoff et al. | 73/602 |
| 4,228,804 | 10/1980 | Holasek et al. | 73/602 |
| 4,322,974 | 4/1982 | Abele et al. | 73/602 |

OTHER PUBLICATIONS

Dines & Kals, "Ultrasonic Attenuation Tomography of Soft Tissues", *Ultrasonic Imaging*, vol. 1, No. 1, 1979, pp. 16-33, Academic Press, Inc.

*Primary Examiner*—Howard A. Birmiel
*Attorney, Agent, or Firm*—Staas & Halsey

[57] ABSTRACT

A method for measuring the physical characteristics of an object through the use of an ultrasonic wave, which comprises the steps of transmitting an ultrasonic pulse to the object, receiving a reflected wave from the object, analyzing the spectrum of a parameter representing the strength of the reflected wave and obtaining a center frequency of the spectrum to measure the physical characteristics of the object. The center frequency is used as a function of distance or time to obtain its differential or difference coefficient, or a computation similar to that for an X-ray computer tomography is carried out, thereby to obtaining an attenuation slope and other data to be used as the physical characteristics of the object.

9 Claims, 3 Drawing Figures

ULTRASONIC MEASURING METHOD

BACKGROUND OF THE INVENTION

1. Field of the Invention

The present invention relates to an ultrasonic measuring method for obtaining physical characteristics of the inside of a subject of measurement by transmitting an ultrasonic wave into the subject, receiving a reflected ultrasonic wave from the inside of the subject and processing the received signal.

2. Description of the Prior Art

Ultrasonic measuring technology has made rapid progress and its application, too, is now broadening from metal flaw detection to medical diagnosis. For such ultrasonic measuring technology an ultrasonic reflection method is employed. The ultrasonic reflection method utilizes the reflection of an ultrasonic wave from the inside of an object at an acoustically heterogeneous point therein, and receives the reflected ultrasonic wave, producing an echogram. The reflected ultrasonic wave is obtained based on the state of the acoustically heterogeneous point, including the influences (attenuation, reflection) on the ultrasonic wave by that portion of the object through which it propagates to the acoustically heterogeneous point. The magnitude of the reflected ultrasonic wave depends largely upon the angle of incidence of the ultrasonic wave to the acoustically heterogeneous point and the state of the surface of the point, and does not exactly indicate physical characteristics of the object, such as an acoustic impedance and so forth.

For this reason, the existing ultrasonic reflection method is used mainly for the indication of the position of the acoustically heterogeneous point, and it cannot be utilized for measuring the physical characteristics of an object (for example, an attenuation characteristic).

Various attempts have been made to broaden the application of such an ultrasonic reflection method. These attempts are disclosed, for instance, in Japanese Patent Application Gazette No. 24798/77 published on July 4, 1977 and Japanese Patent "Kokai"(Laid-Open) Gazette No. 38490/74 laid open on Apr. 10, 1974. These prior art techniques are to measure an absorption coefficient of a substance by transmitting and receiving ultrasonic waves having different frequency components and lessening the influence of the reflections of the ultrasonic waves at a heterogeneous interface in the acoustic path through utilization of the sound pressure ratio of each frequency component to the others.

However, such prior art techniques are effective only when the received reflection intensity is sufficient. In general, in the case where the reflection intensity is insufficient, as the signal to noise ratio approaches unity, the denominator and numerator of the sound pressure intensity ratio may sometimes approach zero independently of each other due to the irregularity of the noise amplitude that will introduce dispersion in the value of the ratio between zero and infinity, resulting in a large error.

SUMMARY OF THE INVENTION

It is therefore an object of the present invention to provide an ultrasonic measuring method with which it is possible to effectively obtain information on the physical characteristics of a subject of measurement from a reflected wave therefrom regardless of the received signal intensity.

Briefly stated, the ultrasonic measuring method of the present invention comprises the steps of sending out an ultrasonic wave to a subject of measurement, receiving a reflected wave therefrom, analyzing the spectrum of a parameter representing the strength of the reflected wave and obtaining a center frequency of the spectrum distribution of the parameter. The center frequency is used to obtain an attenuation slope and other data to be used as the physical characteristics of the subject measured with reference to the center frequency. The center frequency is used as a function of distance and its differential or difference coefficient is obtained, or a computation such as an X-ray CT is carried out, thereby to measure the attenuation slope, etc.

DESCRIPTION OF THE PREFERRED EMBODIMENTS

Keeping in mind the fact that the physical characteristics of a subject of measurement appear mainly in the form of a spectrum of the strength of a ultrasonic wave reflected from the subject, the present invention is intended to measure such physcial characteristics of the subject such as the attenuation slope, the absorption coefficient, the acoustic impedance and the attenuation coefficient, based on a center frequency and the spectral shapes of distribution parameters, etc.

In the following embodiment of the present invention, based on the power (energy) of the reflected wave, there is adopted, as the subject of measurement, a medium in which an attenuation coefficient $\mu$ of the power (energy) of an ultrasonic wave attenuated during propagation in the medium is substantially proportional to the frequency f of the ultrasonic wave, such as a living tissue. The embodiment will be described with respect to measuring, as a physical characteristic of the medium, its proportional coefficient $\alpha(=d\mu/df)$, that is, its attenuation slope, but the present invention is not limited specifically thereto.

Figure 1:
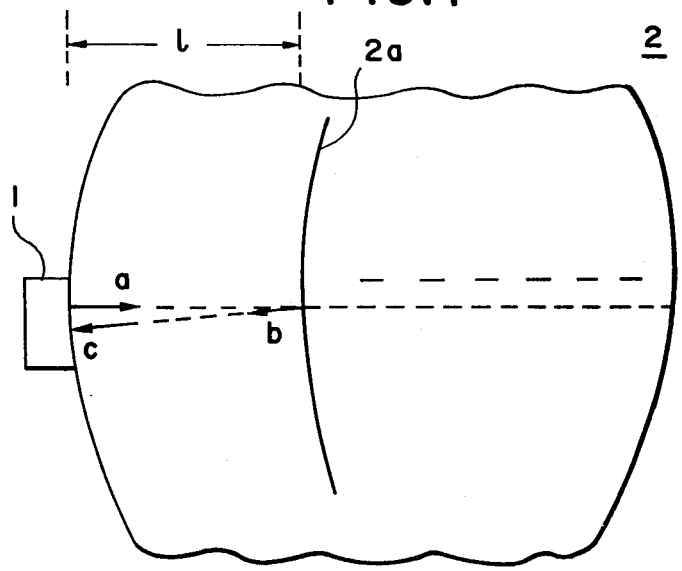
FIG. 1 illustrates the principle of the present invention.
Figure 2:
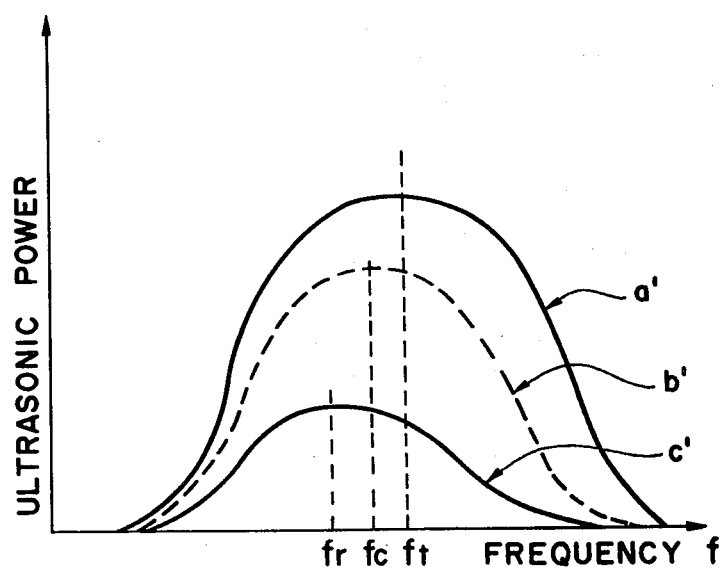
FIG. 2 illustrates a power spectrum distribution.

FIGS. 1 and 2 are explanatory of the principle of the embodiment of the present invention.

In FIG. 1, reference numeral 1 indicates a transducer containing electroacoustic transducer elements such as PZTs or the like; 2 designates an object to be measured, a living tissue in this case; 2a identifies an acoustically heterogeneous interface in the living tissue; a denotes an ultrasonic wave transmitted from the transducer 1; b represents an ultrasonic wave reflected from the acoustically heterogeneous point 2a; and c shows the reflected wave as received by the transducer 1.

The ultrasonic wave a is transmitted from the transducer 1 in such a manner that the spectral distribution of the transmitted signal intensity may become such as indicated by a' in FIG. 2. That is to say, the spectral distribution a' of the transmitted wave a assumes a shape approximated by a Gaussian distribution with a center frequency ft and variance $\alpha$.

The transmission characteristic of the transducer 1 of the ordinary PZT or the like has this distribution characteristic as a whole. In the case of an ultrawide bandwidth transducer as of PVF2 (polyvinylidene fluoride), it suffices to provide a distribution with characteristics as described above by using a drive circuit. This can easily be achieved by including in the drive circuit a filter which yields such a distribution.

The ultrasonic wave thus transmitted with its spectral distribution in the form of the Gaussian distribution is reflected by the acoustically heterogeneous interface 2a as the reflected ultrasonic wave b.

The spectral distribution of the signal intensity of the reflected ultrasonic wave b is as indicated by b' in FIG. 2. The reflected ultrasonic wave c received by the transducer 1 is further attenuated and its spectral distribution becomes as indicated by c' in FIG. 2. The reason for the downward shift in the center frequencies $f_c$ and $f_r$ of these spectral distributions b' and c' as compared to distribution a' is that the higher the frequency of a component, the stronger the component is attenuated. Putting the X-axis on the ultrasonic propagation path from the transducer to the interface, the acoustically heterogeneous point 2a is spaced a distance, x=l, from the transducer 1. Since this distance is a distance over which the time interval between the transmission of the ultrasonic wave a from the transducer 1 and the reception of the reflected ultrasonic wave c by the transducer 1 can be measured, the distance l can easily be measured from this time interval when the velocity of ultrasonic sound in the medium is known.

This time interval measurement is made by using a burst signal or short duration as the transmitted signal and one transducer both for transmission and reception. If a continuous wave or a long waveform is used, then it is necessary to employ transducers individually for transmission and reception. In this case, an ultrasonic wave reflection measurement corresponding to length l can be made by performing phase modulation or the like by using a pseudo-random code or the like.

A detailed description will be given of an example in which the transmitted ultrasonic wave is a short burst wave, i.e. an ultrasonic pulse and one transducer is used as both the transmitter and receiver.

As is well known in the art, the ultrasonic power (energy) of a wave is attenuated exponentially in living tissue or the like.

Now, letting the ultrasonic intensity power after being transmitted over the distance l in the living tissue be represented by I and the transmission intensity power be represented by Io, the following equation holds:

$$I = Io \cdot \exp\left(-\sum_{x=0}^{l} \mu(x) \cdot \Delta x\right) \quad (1)$$

where $\mu$ is an attenuation coefficient which is a generalization of the effects caused by absorption, refraction, reflection and scattering by the living tissue, and the intensity power is a quantity proportional to the square of the sound pressure for a single frequency component.

On the other hand, the attenuation coefficient $\mu$ is expressed by a linear function of the frequency f of the ultrasonic wave as follows:

$$\mu = \mu_0 + \alpha \cdot f \quad (2)$$

where $\mu_0$ is a constant independent of the frequency and $\alpha$ is the attenuation slope for the frequency.

Now, when transmitting an ultrasonic signal with the power spectral distribution indicated by a' in FIG. 2, the signal propagates the distance l in the living tissue and is subjected to attenuation as expressed by Eqs. (1) and (2), yielding an ultrasonic signal of the power spectral distribution indicated by b' in FIG. 2. The spectral distribution of this signal is the Gaussian distribution as is the case with the transmitted ultrasonic signal a', but the center frequency shifts downward to $f_c$. However, the variance remains unchanged and is kept at $\sigma$ the same as the transmitted ultrasonic signal.

The variance $\sigma$, the center frequencies $f_t$ and $f_c$ and the absorption coefficient bear the following relation:

$$\frac{1}{\sigma^2}(f_t - f_c) = \sum_{x=0}^{l} \alpha(x) \cdot \Delta x \quad (3)$$

This relation is set forth in an article by A. C. Kak and K. A. Dines on page 26 of "ULTRASONIC IMAGING", Vol. 1, No. 1, Academic Press, 1979.

Eq. (3) does not include the transmission factors for the acoustically heterogeneous interfaces lying scattered in the ultrasonic propagation path along the distance l and the absolute value of the signal intensity, and it indicates that the ultrasonic wave signal is entirely free from their influences.

Now, consider a signal reflected from the position 2a at the distance l from the transmitter. Since it is assumed that the reflection coefficient at the acoustically heterogeneous point has no frequency dependence, the intensity of each frequency component in the spectral distribution of the reflected signal from the point 2a becomes such that the intensity of each frequency component of the incident signal at the point 2a decreases at a fixed rate, but the center frequency and variance remain unchanged.

Accordingly, the spectral distribution shape of the reflected wave b from the acoustically heterogeneous point similarly becomes as indicated by b' in FIG. 2.

The reflected wave b is propagated towards the transducer 1 in a direction reverse to that when transmitted, but it is subjected to the same attenuation as in the transmission path. As a result, the reflected wave b is received by the transducer 1 as a signal having the spectral distribution indicated by c' in FIG. 2. The reflected signal c assumes the Gaussian distribution as is the case with reflected wave b; therefore, the center frequency shifts downwards to $f_r$ and variance is held at $\sigma$.

Accordingly, the following equation holds as in the case of Eq. (3):

$$\frac{1}{\sigma^2}(f_c - f_r) = \sum_{x=l}^{0} \alpha(x) \cdot \Delta x \quad (4)$$

Eliminating $f_c$ from Eqs. (3) and (4), the following equation is obtained:

$$\frac{1}{2\sigma^2}(f_t - f_r) = \sum_{x=0}^{l} \alpha(x) \cdot \Delta x \quad (5)$$

The right side of Eq. (5) is a line integral of the power attenuation slope.

Next, a description will be given of methods for obtaining $\alpha(x)$ from Eq. (5).

A first method is one that employs an absorption coefficient reproducing algorithm technique is known X-ray computer tomography. With this method, the quantities in Eq. (5), that is, the center frequencies $f_t$ and $f_r$, are measured over the distance l (which can be specified in the reflection method) to the farthest boundary of the measurement region of the living body in as many directions as possible, and a distribution image of the absorption coefficient $\alpha(x,y)$ is reproduced by a computer. The right side of Eq. (5) is exactly the same type as a quantity known as a projection in the X-ray computer tomography, as the distribution image of the absorption coefficient $\alpha(x, y)$ can be used in reproducing the absorption coefficient $\mu(x, y)$ by the X-ray computer tomography method.

In the transmission type ultrasonic computer tomography based on Eq. (3) proposed by the aforementioned A. C. Kak et al., an image corresponding to the case where the attenuation slope a, in an abnormal portion of the living body in which the waves cannot be transmitted due to a bone, is assumed to be zero, can also be reproduced by the algorithm of the transmission type computer tomography through using, as a projection of the unknown portion, the sum of line integrals in portions on both sides of the untransmissible portion, obtained by Eq. (5) using the reflection method of the present invention, instead of using the projection of the untransmissible portion.

Next, a second method will be described.

Now, assuming that acoustically heterogeneous points are continuously distributed at regular intervals $\Delta l$, a received signal reflected from a point $l + \Delta l$ is obtained from Eq. (5) as follows:

$$\frac{1}{2\sigma^2}\{f_t - (f_r - \Delta f_r)\} = \sum_{x=0}^{l+\Delta l} \alpha(x) \cdot \Delta x \quad (6)$$

Subtracting Eq. (5) from Eq. (6), the following equation is obtained:

$$\frac{1}{2\sigma^2} \Delta f_r = \alpha(l) \cdot \Delta l$$

Therefore, $\alpha(l) = \frac{1}{2\sigma^2} \cdot \frac{\Delta f_r}{\Delta l} \quad (7)$ Accordingly, the value of $\alpha(l)$, the attenuation slope, at the depth l can be obtained.

The center frequency of the received power spectrum can be measured by high-speed signal processing, such as real time FFT (Fast Fourier Transformation), using a high-speed pipeline computer or the like instantly or after a certain short period of time, and since $$\Delta l = v \Delta t \quad (8)$$

, where $v$ is the velocity of sound, Eq. (7) becomes as follows:

$$\alpha(l) = \frac{1}{2\sigma^2 v} \cdot \frac{\Delta f_r}{\Delta t} \quad (9)$$

That is to say, variations in the center frequency can be obtained in real time by differentiation with respect to time.

In both cases of Eqs. (7) and (9), the distribution of $\alpha$ on a scanning line is measured by scanning based on one transmission and reception, so that a distribution diagram of $\alpha$ can be obtained in real time. Needless to say, the measurement accuracy can be increased statistically through using a mean value of $\alpha$ obtained by carrying out the scanning n times.

In the case where this $\alpha(l)$ is obtained with respect to coordinate points (x,y) within the range of measurement in an X-Y plane through using ultrasonic beams in various directions, even if $\alpha$ has anisotropy as in the case of muscles, new information concerning the physical characteristics such as the mean value, the direction and degree of anisotropy and so forth can be obtained.

Moreover, when using the first and second methods in combination, average information based on the assumption that the living tissue is isotropic is obtained with the first method and local information in a specified direction can be obtained with the second method and, by comparison processing of both sets of information, useful physical characteristic information can be obtained.

Thus, in the present invention, the absolute value of signal intensity is not necessary and the amplification of the received signal reflected at each depth within the subject of measurement can be set arbitrarily by what is called a TGC (Time Gain Control) circuit or the like, therefore, an excellent signal to noise ratio can always be maintained. Furthermore, since a calculation which is liable to introduce an error, such as for obtaining a ratio at a low signal level, is not involved and since distribution parameters such as the center frequency, variance and so forth are measured from a large quantity of information based on the spectral distribution, the measurement accuracy can be raised statistically. Incidentally, noise in the entire measurement system can be regarded as having a white noise type spectrum, and hence has little influence on the measurement of the center frequency.

Figure 3:
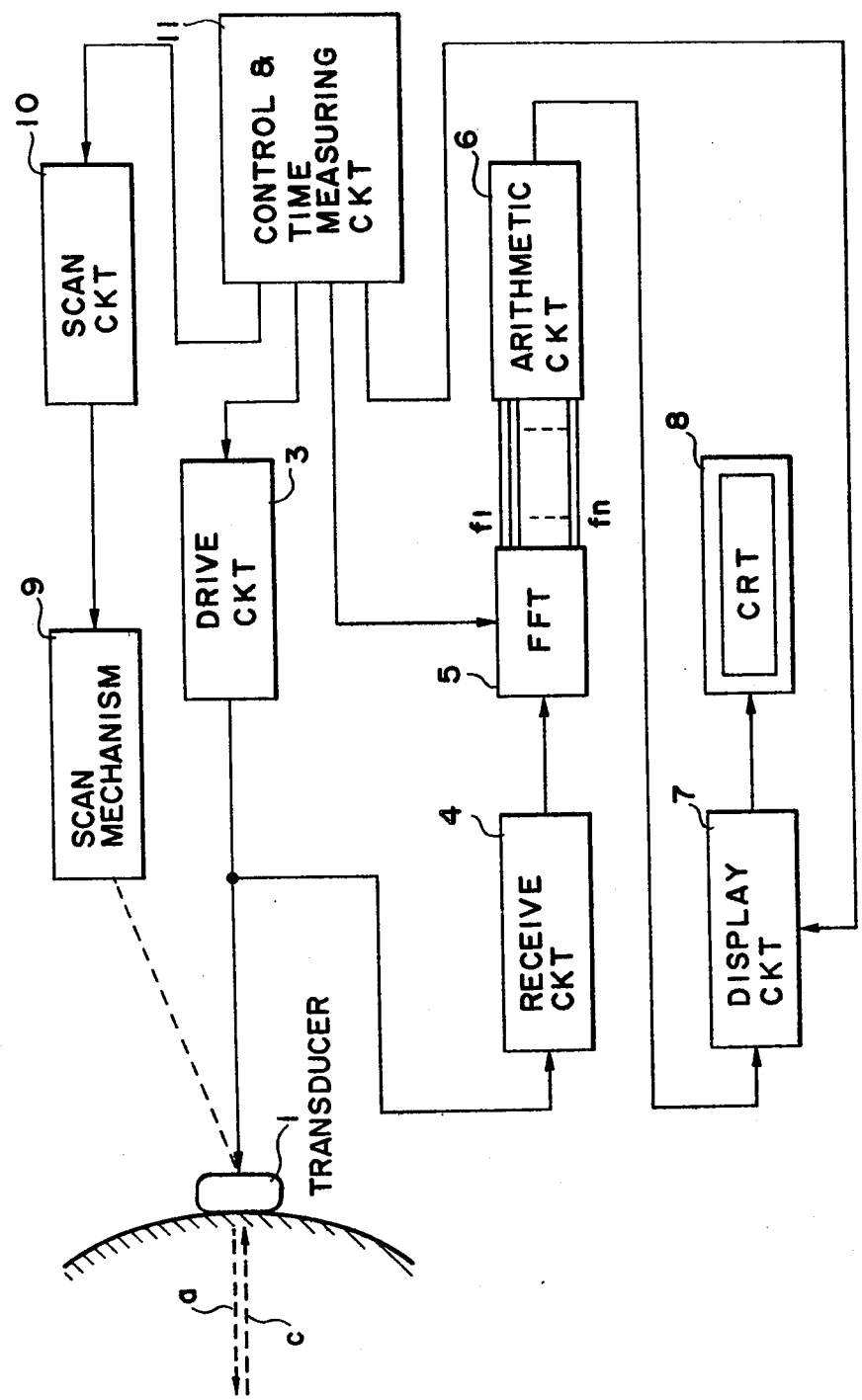
FIG. 3 is a block diagram illustrating an apparatus for use in an embodiment of the present invention.

Next, a description will be given, with reference to FIG. 3, of the arrangement for carrying the method of the present invention into practice.

Reference numeral 1 indicates a transducer for transmission and reception. A transmitter transducer can be formed by a PZT or PVF2 element and a receiver transducer can be formed by a CdS element. The PZT and the PVF2 element can be used both for transmission and reception and, in the case of using the CdS element, it is disposed in the vicinity of the transmitter transducer. Reference numeral 3 designates a drive circuit, in which can be incorporated, as required, a filter or the like for producing the Gaussian distribution; and 4 identifies a receive circuit which, in the case of using as the transducer the PZT or PVF2 element, includes an orthogonal multiplier circuit for converting sound pressure into power and the so-called TGC (Time Gain Control) circuit for compensating for attenuation during propagation in the living body. When the receiver transducer 1 is the CdS element having a power output, the above-said orthogonal multiplier circuit is omitted. Reference numeral 5 denotes an FFT (Fast Fourier Transform) circuit, which usually includes an A/D converter and a digital arithmetic circuit. In many cases, the function of the above-mentioned orthogonal multiplier circuit is performed in this circuit rather than in the receive circuit 4. Reference numeral 6 shows an arithmetic circuit, when comprises a microcomputer, a memory and so forth. The arithmetic circuit 6 receives the intensity of each frequency component from the FFT circuit 5, computes the center frequencies $f_c$ and $f_r$ and the variance $\sigma$, computes Eq. (5) under program control and obtains the line integral of the power attenuation slope for each scanning line, thereby carrying out the image reproduction according to the first method. In the case of the second method, the arithmetic circuit 6 is able to calculate Eq (7) or (9) under program control. Reference numeral 7 refers to a display circuit for displaying on a CRT 8 the distribution image of α thus obtained. Reference numeral 9 indicates the scan mechanism of a motor or like mechanical transmission structure for changing the direction or position of scanning of the transducer, which mechanism is driven by a scan circuit 10. Incidentally, it is also possible to perform measurement from many directions and positions by using a multi-segment type transducer instead of the transducer 1, the scan mechanism 9 and the scan circuit 10, performing linear or sectorial electron scanning through the use of a phased array of electronically controlled drive phases and mechanically shifting the position of the transducer. Reference numeral 11 designates a control and time measuring circuit, which has incorporated therein a clock generator and controls the operation sequence of the respective circuits mentioned above and, at the same time, measures the time interval between the transmission of each ultrasonic wave and the reception of each reflected ultrasonic wave. The circuit 11 may also be incorporated in the arithmetic circuit 6.

The abovesaid components are already well-known and this indicates that the present invention can easily be practised.

While in the foregoing the present invention has been described in connection with the power spectrum, in particular, the Gaussian distribution, the invention is also applicable to other factors such as the shape of the spectral distribution of sound pressure, sound pressure within the duration of a burst wave and a temporarily integrated value of power.

Furthermore, in the case of a non-Guassian distribution, the deviation of the spectral distribution of a transmitted and received signal from the Gaussian distribution or asymmetry of both hands higher and lower than the center frequency may also be an object of measurement.

Also in these cases, the same results as described in the foregoing can be obtained since measurement is not affected by the absolute value of signal intensity.

As has been described in the foregoing, according to the present invention, since the physical characteristics are measured from the intensity spectrum of a reflected wave, the medium characteristic parameters of an internal structure of a living tissue or the like can be measured with high accuracy of their distribution diagrams can be obtained without being affected by the transmission factors and the reflection factors at boundaries between respective portions of the medium and without introducing an error even when there is a region of low reflected signal intensity. By one scanning, parameters on the scanning line can also be obtained, so that real time measurement can be effected. Thus, the present invention offers an ideal measuring method, coupled with the convenience of use which originates in the reflection method.

It will be apparent that many modifications and variations may be effected without departing from the scope of the novel concepts of the present invention.

What is claimed is:

1. An ultrasonic measuring method, comprising the steps of:
   transmitting an ultrasonic pulse to an object;
   receiving a reflected wave from said object;
   analyzing the spectrum of a parameter representing the strength of said reflected wave at a plurality of predetermined times; and
   obtaining a center frequency by the analysis of said spectrum and obtaining an attenuation slope and other parameter coefficients corresponding to the physical characteristics of said object from said center frequency for each of the predetermined times;
   wherein said center frequency obtained at each of the predetermined times is used as a function of time to obtain its variance, obtaining said attenuation slope and said other parameter coefficients.

2. An ultrasonic measuring method according to claim 1, wherein said ultrasonic pulse transmitting step, said reflected wave receiving step and said reflected wave analyzing step are repeated a plurality of times the spectra of the parameters representing the strength of the reflected wave thus obtained are averaged by statistical processing, and the physical characteristics of said object are measured from said averaged spectrum.

3. An ultrasonic measuring method according to claim 1, wherein said ultrasonic pulse transmitting step, said reflected wave receiving step and said reflected wave analyzing step are carried out from different points in accordance with scanning of said object, and by analyzing the spectrum of said parameter representing the strength of said reflected wave obtained by said scanning, a distribution diagram of the physical characteristics of said object is generated.

4. An ultrasonic measuring method, comprising the steps of:
   transmitting an ultrasonic pulse to an object;
   receiving a reflected wave from said object;
   analyzing the spectrum of a parameter representing the strength of said reflected wave at a plurality of predetermined times; and
   obtaining a center frequency by the analysis of said spectrum to obtain an attenuation slope and other parameter coefficients corresponding to the physical characteristics of said object from said center frequency for each of the predetermined times;
   wherein said ultrasonic pulse transmitting step, said reflected wave receiving step and said reflected wave analyzing step are carried out in plurality of directions with respect to said object and a distribution diagram of the physical characteristics of said object is obtained by analyzing the spectrum of said parameter representing the strength of said reflected wave in each direction and for each of the predetermined times.

5. An ultrasonic object measuring method, comprising the steps of:
   (a) transmitting an ultrasonic pulse;
   (b) sampling reflected waves at predetermined time intervals;
   (c) calculating a power spectrum of each of the reflected waves;
   (d) determining a center frequency of the power spectrum for each of the reflected waves; and
   (e) determining an attenuation slope as a function of time based on the center frequency of each of the sampled reflected waves.

6. An ultrasonic object measuring method according to claim 5, further comprising the steps of:
   (f) transmitting another ultrasonic pulse;
   (g) receiving other reflected waves;

(h) calculating power spectrums of the other reflected waves; and (i) calculating an average power spectrum.

7. An ultrasonic object measuring method according to claim 6, wherein the another ultrasonic pulse is transmitted from a different point, and wherein said method further comprises the steps of:

(j) determining an attenuation slope for the different point; and (k) generating a distribution diagram.

8. An ultrasonic object measuring method according to claim 7, further comprising determining absorption coefficients, attenuation coefficients, and an accoustic impedances of the object.

9. An ultrasonic object measuring method according to claim 8, wherein said ultrasonic pulses have a guassian spectral distribution.

* * * * *

UNITED STATES PATENT AND TRADEMARK OFFICE
CERTIFICATE OF CORRECTION

PATENT NO. : 4,452,082

DATED : June 5, 1984

INVENTOR(S) : Hirohide Miwa

It is certified that error appears in the above-identified patent and that said Letters Patent is hereby corrected as shown below:

Column 1, line 32, "an" should be --the--.

Column 2, line 29, "a" second occurrence should be --an--;
          line 54, "a" should be --$\bar{a}$--;
          line 55, "b" should be --$\bar{b}$--;
          line 57, "c" should be --$\bar{c}$--;
          line 59, "a" should be --$\bar{a}$--;
          line 62, "a'" should be --$\bar{a}'$--;
          line 63, "$\bar{a}$'" should be --$\bar{a}'$--;
                    "a" should be --$\bar{a}$--;
          line 65, "$\alpha$" should be --$\bar{\sigma}$--.

Column 3, line 9, "b" should be --$\bar{b}$--;
          line 11, "b" should be --$\bar{b}$--;
          line 12, "c" should be --$\bar{c}$--;
          line 14, "c'" should be --$\bar{c}'$--;
          line 16, "these" should be --the--;
                    "b'" should be --$\bar{b}'$--;
                    "c'" should be --$\bar{c}'$--;

UNITED STATES PATENT AND TRADEMARK OFFICE
CERTIFICATE OF CORRECTION

PATENT NO. : 4,452,082                    Page 2 of 2
DATED      : June 5, 1984
INVENTOR(S): Hirohide Miwa It is certified that error appears in the above-identified patent and that said Letters Patent is hereby corrected as shown below:

line 20,    after "transducer", insert --1--;
           line 24,    "a" should be --$\underline{a}$--;
           line 25,    "c" should be --$\underline{c}$--;
           line 26,    "can easily be" should be --can be easily--.

Column 4, line 36,    "b" should be --$\underline{b}$--;
           line 37,    "b'" should be --$\underline{b}'$--;
           line 38,    "b" should be --$\underline{b}$--;
           line 41,    "b" should be --$\underline{b}$--;
           line 43,    "c'" should be --$\underline{c}'$--;
           line 44,    "c" should be --$\underline{c}$--.

Column 5, line 9,     "as" should be --and--;
           line 16,    "a" should be --$\alpha$--;
           line 59,    "formula (9)), "$\alpha(1)$" should be --$\overline{\alpha(1)}$--.

Column 6, line 62,    "when" should be --which--.
Column 7, line 39,    "hands" should be --bands--;
           line 50,    "of" should be --or--.

Signed and Sealed this

Twenty-fifth Day of December 1984

[SEAL]

Attest:

GERALD J. MOSSINGHOFF

Attesting Officer    Commissioner of Patents and Trademarks